US000001989B1

(19) United States

(12) Statutory Invention Registration

Fell et al.

(10) Reg. No.: US H1989 H

(43) Published: Sep. 4, 2001

(54) MICROPOROUS FILMS HAVING ZONED BREATHABILITY

(75) Inventors: David Arthur Fell, Neenah; Sarah Jane Marie Freiburger, Kaukauna; Keith Joseph Renard, Oshkosh, all of WI (US)

(73) Assignee: Kimberly-Clark Worldwide, Inc., Neenah, WI (US)

(21) Appl. No.: 09/312,426

(22) Filed: May 14, 1999

(51) Int. Cl.[7] ..... B32B 31/00; B29C 47/00; B29C 65/00; B29C 59/00

(52) U.S. Cl. ..... 156/229; 156/244.24; 156/280; 264/41; 264/129; 264/210.6; 427/207.1

*Primary Examiner*—Charles T. Jordan
*Assistant Examiner*—Aileen J. Baker

(74) *Attorney, Agent, or Firm*—Kimberly-Clark Worldwide, Inc.

(57) ABSTRACT

Breathable microporous films are provided having controlled regional breathability with high WVTR regions and thicker low WVTR regions. The zoned breathable microporous films are be made by selectively applying adhesive to the microporous film.

13 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MICROPOROUS FILMS HAVING ZONED BREATHABILITY

FIELD OF THE INVENTION

The present invention relates to absorbent articles incorporating breathable microporous films. More particularly, the present invention relates to breathable microporous films having zoned breathability and methods of making the same.

BACKGROUND OF THE INVENTION

Various types of garments are presently available for absorbing human discharge. Examples of these garments include baby diapers, feminine care products, incontinence garments and the like. Generally speaking, the basic structure of this class of garments requires an aqueous liquid pervious body-side liner, an absorbent pad ail containing one or more layers for receiving and absorbing the discharge, and an aqueous liquid impervious backing member for containing the discharge. Such garments usually include a film material that serves as an aqueous liquid impervious outer cover. However, such film material lacks breathability, causing the undergarments to be hot and uncomfortable.

Microporous films are "breathable" barriers in the sense that the film acts as a barrier to aqueous liquids and particulate matter but allows water vapor and air to pass therethrough. In addition, by achieving and maintaining high breathability it is possible to provide an article that is more comfortable to wear since the migration of water vapor through the fabric helps reduce and/or limit discomfort resulting from excess moisture trapped against the skin. Thus, such an article can potentially contribute to an overall improved skin wellness.

Accordingly, microporous films have become an important article of commerce, finding a wide variety of applications. For example, microporous films have been used as outer covers for personal care products such as diapers, training pants, incontinence garments, feminine hygiene products and the like. In addition, microporous films have likewise found use in protective apparel and infection control products such as surgical gowns, surgical drapes, protective workwear, wound dressings and bandages. Often microporous films are utilized as a multilayer laminate. The films can provide the desired barrier properties to the article while other materials laminated thereto can provide additional characteristics such as strength, abrasion resistance and/or softness and drapability. For example, fibrous webs such as non-woven fabrics allow the laminate to retain its breathability and can provide additional strength as well as an article having a cloth-like feel. Thus, microporous film laminates can be used in a variety of applications including, for example, those described above.

Although the breathability provided by microporous films and/or laminates thereof is advantageous in many articles, there exist some situations where high breathability can be undesirable. For example, in absorbent personal care articles such as diapers or incontinence garments designed to absorb and contain aqueous liquid human exudates the breathable barrier and absorbent core generally work together to retain bodily fluids discharged into the garment. However, when fluid (aqueous liquid) is retained within the absorbent core significantly higher amounts of water vapor begin to pass through the breathable barrier. The increased amounts of water vapor passing through the outer cover can form condensate on the outer portion of the garment. The condensate is simply water but can be perceived by the wearer as leakage. In addition, the condensate can create a damp uncomfortable feel to the outer portion of the garment which is unpleasant for those handling the article. It is believed that the skin wellness and/or improved comfort benefits of breathable outer covers are not achieved at areas directly adjacent the portion of the absorbent core retaining considerable mounts of aqueous liquid (e.g. typically those areas of the central or crotch region of he garment). Providing a breathable barrier which has less or limited breathability in such regions, while providing good breathability in the remaining regions, would provide a garment with excellent wearer comfort yet which limits the potential for outer cover dampness. Thus, a breathable barrier that provides either zoned or controlled regional breathability is highly desirable.

Therefore, there exists a need for a breathable microporous film having regions with varied levels of breathability. In addition, there exists a need for such films which retain the desired barrier properties and which are capable of lamination to additional materials. Further, there exists a need for methods of making such films and in particular methods of reliably obtaining the desired levels of breathability in distinct regions of a film.

Thus, it becomes apparent that a need exists for an absorbent undergarment, diaper training pants or the like, that exhibits desired absorbency and containment characteristics of absorbent garments, such as undergarments, while improving comfort during use.

SUMMARY OF THE INVENTION

The aforesaid needs are fulfilled and the problems experienced by those skilled in the art overcome by the film of the present invention which, in one aspect, comprises a first microporous region having a thickness less than 100$\mu$ and a WVTR of at least 800 g/m$^2$/24 hours and a second region having a WVTR (also referred to as porosity) less than that of the first region wherein the WVTR of the second region is at least 15% less than the WVTR of the first region. The film has a hydrohead of at least about 50 mbar. The second region desirably has minimum dimensions of 5 cm by 5 cm and still more desirably comprises from about 5% to about 75% of the area of said film. In a further aspect, the first region can have a WVTR in excess of about 2500 g/m$^2$/24 hours and the second region a WVTR less than about 1500 g/m$^2$/24 hours. Additionally and/or alternatively, the second region can have a WVTR at least about 50% less than the WVTR of the first region. Further, the film can comprise a third region having a WVTR intermediate to that of the first and second regions. Still further, the film can comprise primarily a thermoplastic polymer and in a further aspect, can comprise at least about 40% by weight filler and a thermoplastic polymer.

In a further aspect of the invention, the methods of making films having regions of varied breathability are provided and can comprise providing a microporous film having a hydrohead of at least 50 mbars and a WVTR of at least 800 g/m$^2$/24 hours and then selectively applying adhesives to a selected portion of said film thereby creating first and second regions therein. The WVTR is decreased within the second region of the microporous film, i.e. the selected portion to which meaningful adhesives have been applied, relative to the WVTR of the first region. The second region can have minimum dimensions of at least 5 cm by 5 cm and desirably the second region comprises from about 5% to about 75% of the area of said film. In a preferred embodiment, adhesive is selectively applied to the microporous film such that a pattern, continuous or discontinuous, of the second region is produced on the film.

Further aspects of the present invention will appear in the description hereinafter.

DEFINITIONS

As used herein the term "nonwoven" fabric or web means a web having a structure of individual fibers or threads which are interlaid, but not in an identifiable manner as in a knitted or woven fabric. Nonwoven fabrics or webs have been formed by many processes such as for example, meltblowing processes, spunbonding processes, hydroentangling, air-laid and bonded carded web processes.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 338,992 and 3,341,394 to Kinney, U.S. Pat. No. 3,502,763 to Hartman, U.S. Pat. No. 3,542,615 to Dobo et al, U.S. Pat. No. 5,382,400 to Pike et al., and U.S. Pat. No. 5,759,926 to Pike et al. Spunbond fibers are generally not tacky when they are deposited onto a collecting surface and are generally continuous.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers may be continuous or discontinuous, are generally smaller than 10 microns in average diameter, and are generally tacky when deposited onto a collecting surface.

As used herein "multilayer nonwoven laminate" means a laminate of two or more nonwoven layers such as, for example, wherein some of the layers are spunbond and some meltblown such as a spunbond/meltblown/spunbond(SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein, the term "machine direction" or MD means the length of a fabric in the direction in which it is produced. The term "cross machine direction" or CD means the width of fabric, i.e. a direction generally perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, "ultrasonic bonding" means a process performed, for example, by passing the fabric between a sonic horn and anvil roll as illustrated in U.S. Pat. No. 4,374,888 to Bornslaeger.

As used herein "point bonding" means bonding one or more layers of fabric at numerous small, discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen et al.

As used herein, the term "barrier" means a film, laminate or other fabric which is relatively impervious to the transmission of aqueous liquids and which has a hydrohead of at least about 50 mbar. Hydrohead as used herein refers to a measure of the aqueous liquid barrier properties of a fabric measured in millibars (mbar) as described herein below. However, it should be noted that in many applications of barrier fabrics, it may be desirable that they have a hydrohead value greater than about 80 mbar, 150 mbar or even 200 mbar.

As used herein, the term "breathability" refers to the water vapor transmission rate (WVTR) of an area of fabric which is measured in grams of water per square meter per 24 hours ($g/m^2/24$ hours). The WVTR of a fabric is the water vapor transmission rate which, in one aspect, gives an indication of how comfortable a fabric would be to wear. WVTR can be measured as indicated below and the results are reported in grams/square meter/24 hours.

As used herein the term "monocomponent" fiber refers to a fiber formed from one or more extruders using only one polymer. This is not meant to exclude fibers formed from one polymer to which additives have been added. As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers of a multicomponent fiber are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea" type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers and methods of making them are also taught in U.S. Pat. No. 5,382,400 to Pike et al. and may be used to produce crimp in the fibers by using the differential crystallization properties of the two (or more) polymers. The fibers may also have various shapes such as those described in U.S. Pat. Nos. 5,277,976 to Hogle et al., U.S. Pat. No. 5,466,410 to Hills and 5,069,970 and 5,057,368 to Largman et al.

As used herein the term "blend" means a mixture of two or more polymers while the term "alloy" means a sub-class of blends wherein the components are immiscible but have been compatibilized.

As used herein the term "biconstituent fibers" or "multiconstituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Bicomponent and biconstituent fibers are discussed in U.S. Pat. No. 5,294,482 to Gessner and in the textbook *Polymer Blends and Composites* by John A. Manson and Leslie H. Sperling, copyright 1976 by Plenum Press, a division of Plenum Publishing Corporation of New York, ISBN 0-306-30831-2, at pages 273 through 277.

As used herein, the term "scrim" means a lightweight fabric used as a backing material. Scrims are often used as the base fabric for coated or laminated products.

As used herein, the term "garment" means the same as the term "personal care product".

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets and the like.

As used herein, the term "personal care product" means personal hygiene oriented items such as diapers, training pants, absorbent underpants, adult incontinence products, feminine hygiene products, and the like.

As used herein the term "backsheet" refers to the aqueous liquid impervious protective layer on the garment side of a personal care product which prevents bodily exudates from escaping from the product.

As used herein, the term "protective cover" means a cover for vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths, picnic area covers, tents and the like.

DETAILED DESCRIPTION OF THE INVENTION

Figure 1A:
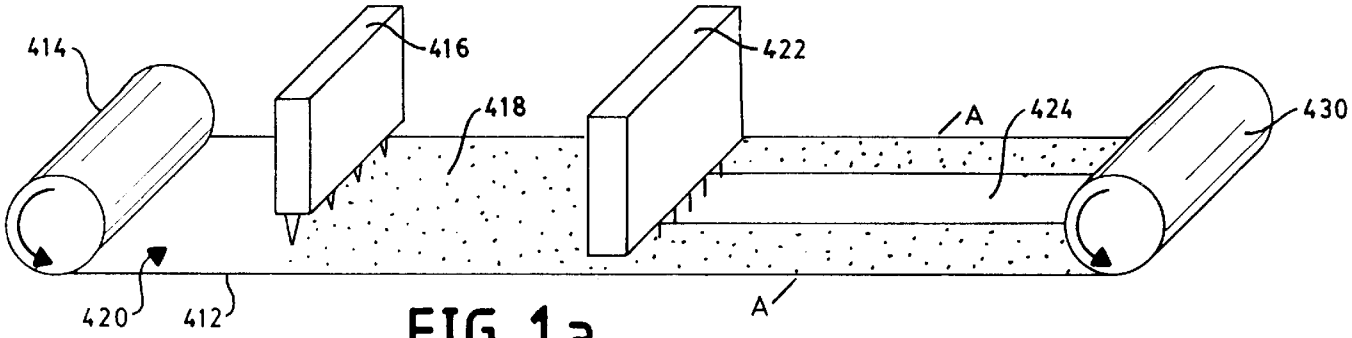
FIG. 1*a* is a schematic representation of an exemplary adhesive applicator assembly suitable for use in practicing the present invention and a zone treated film made therefrom.

A breathable microporous film 412 can be treated, in accord with the present invention, to create a breathable film which can be used as a backsheet for personal care products, having regions of varied breathability using adhesives or other coating materials. The term "adhesive" or "adhesives" as used herein includes, but is not limited to, any material which will adhere to the microporous film when applied by some coating apparatus, thereby reducing the WVTR of the microporous film where the adhesive has been applied. In reference to FIGS. 1*a* and 1*b* microporous film 412 is unwound from supply roll 414. A adhesive applicator 416 delivering an open patterned application, including but not limited to a Nordson Control Coat CC-200 available from the Nordson Corporation at Norcross, Ga., applies a construction adhesive layer 418 to the body-side surface 420 of the microporous film 412. The construction adhesive layer 418 is applied in an open pattern and as such, has minimal effect on the breathability of the microporous film 412. A second adhesive applicator 422, including but not limited to a Nordson EP45 contact type coating head available from the Nordson Corporation at Norcross, Ga., is pulsed to apply an adhesive coat layer 424 on to areas where less breathability is desired. The amount of adhesive applied in the adhesive coat layer 424 depends on the desired reduction in breathability. The adhesive coat layer 424 applied to the microporous film 412 at least partially covers or fills the pores within the microporous film 412, thereby reducing the size or number of pores within microporous film 412 thereby reducing the breathability of the film in these selected areas.

Figure 2B:
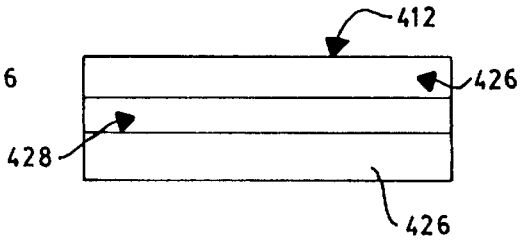
FIG. 2*b* is a plan view of a zone treated microporous film suitable for use in a practicing the present invention.
Figure 2A:
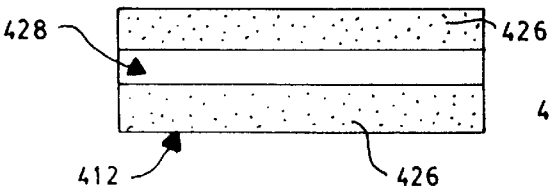
FIG. 2*a* is a plan view of a zone treated microporous film suitable for use in a practicing the present invention.

Thus, a breathable microporous film 412 can be made having regions of controlled breathability. As shown in FIGS. 2*a* and 2*b* a microporous film 412 is created having a first breathable regions 426 and second regions 428 having a breathability or WVTR lower than that of the first regions 426. The treated film 412 can then be wound on a winder roll 430 or further processed or converted as desired.

The construction adhesive layer 418 can be applied over the entire body-side surface 420 of the microporous film 412 or the construction adhesive layer 418 can be applied in the areas only where the adhesive coat layer 424 will not be applied. The construction adhesive layer 418 is typically a construction adhesive, the adhesive used to attach the various components of product into which the microporous film 412 is incorporated. The construction adhesive layer 418 preferably is from about 1 gsm to about 7 gsm, more preferably from about 2 gsm to about 5 gsm, and most preferably 3.2 gsm. An example of a construction adhesive is 34-5610 from National Starch and Chemical Company in Bridgewater, N.J.

In another embodiment of the present invention, a breathable microporous film 412 can be treated, in accord with the present invention, to create a breathable film having regions of varied breathability using adhesives. In reference to FIGS. 1*a* and 1*b,* microporous film 412 is unwound from supply roll 414. An adhesive applicator 422, including but not limited to a Nordson EP45 contact type coating head available from the Nordson Corporation at Norcross, Ga., is pulsed to apply an adhesive coat layer 424 on to areas where less breathability is desired. The amount of adhesive applied in the adhesive coat layer 424, as well as the type of adhesive and the type of adhesive application, determines the desired reduction in breathability. The adhesive coat layer 424 applied to the microporous film 412 at least partially covers or fills the pores within the microporous film 412, thereby reducing the size or number of pores within microporous film 412 thereby reducing the breathability of the film in these selected areas. Thus, a breathable microporous film 412 can be made having regions of controlled breathability. As shown in FIGS. 2*a* and 2*b,* a microporous film 412 is created having a first breathable regions 426 and second regions 428 having a breathability or WVTR lower than that of the first regions 426. The treated film 412 can then be wound on a winder roll 430 or further processed or converted as desired.

While it may be typical to apply the adhesive coat layer 424 to the body-side surface 420 of the microporous film 412, the adhesive coat layer 424 may be applied to the garment-side surface 421 of the microporous film 412 as it is incorporated into absorbent garments. The garment side surface 421 of the microporous film refers to the surface of the microporous film 412 that will face away from the wearer, toward the wearer's clothes when the microporous film 412 is incorporated into the breathable absorbent garment.

Suitable microporous films for practicing this embodiment of the present invention include breathable microporous films having a WVTR of at least 800 $g/m^2/24$ hours, and more desirably having a WVTR in excess of 1500 $g/m^2/24$ hours, 2500 $g/m^2/24$ hours or 3500 $g/m^2/24$ hours. Desirably, the breathable microporous film substrate has a WVTR between about 2000 $g/m^2/24$ hours and about 7000 $g/m^2/24$ hours. The breathable microporous films preferably have a film thickness less than about 100$\mu$ (microns) and desirably have a thickness less than about 50$\mu$ and more desirably have a thickness between about 10 and about 35$\mu$. Thin breathable microporous film can be formed by any one of various methods known in the art. Examples of microporous films suitable for use with the present invention include, but are not limited to, those described in the following references. U.S. Pat. No. 5,800,758 issued Sep. 1, 1998 to Topolkaraev et al.; U.S. Pat. No. 4,777,073 issued Oct. 11, 1988, to Sheth; and, U.S. Pat. No. 4,867,881 issued Sep. 19, 1989, to Kinzer; the entire contents of the aforesaid references are incorporated herein by reference.

Additional examples of microporous films suitable for use with the present invention include, but are not limited to, those described in the following references: U.S. Pat. No. 4,613,544 issued Sep. 23, 1986, to Burleigh; U.S. Pat. No. 4,833,026 issued May 23, 1989, to Kausch; U.S. Pat. No. 4,863,788 issued Sep. 5, 1989, to Bellairs et al.; U.S. Pat. No. 4,878,974 issued Nov. 7, 1989, to Kagawa; U.S. Pat. No. 4,620,956 issued Nov. 4, 1986,to Hamer; U.S. Pat. No. 4,620,955 issued Nov. 4, 1986, to Kono et al.; and, U.S. Pat. No. 5,352,513 issued Oct. 4, 1994, to Mrozinski et al.; the entire contents of the aforesaid references are incorporated herein by reference.

A preferred breathable microporous film can comprise a stretched-filled film which includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. The thermoplastic polymer and filler can be stretched in at least one direction, thereby reducing the film gauge or thickness and creating a network of micropores throughout the film of a size and frequency to achieve the desired level of breathability. Such films, prior to stretching, desirably have a basis weight of less than about 100 $g/m^2$ and even more desirably less than about 60 $g/m^2$. Upon stretching, the multilayer film desirably has a basis weight of less than about 60 $g/m^2$ and even more desirably between about 15 and 35 $g/m^2$. Suitable films can also include multilayer films having at least one microporous layer such as, for example, those described in the references cited above.

The microporous films can comprise known film forming polymers which are, by mechanical and/or thermal treatment, permanently deformable. Mechanically deformable polymer films are believed to be suitable for use with the present invention (e.g. soft rubbers). Desirably the microporous film is made from a thermoplastic polymer. Preferred thermoplastic polymers used in the microporous films of the present invention include, but are not limited to, polyolefins including homopolymers, copolymers, terpolymers and blends thereof. Additional film forming polymers suitable for use with the present invention, alone or in combination with other polymers, include ethylene vinyl acetate, ethylene ethyl acrylate, ethylene acrylic acid, ethylene methyl acrylate, ethylene normal butyl acrylate, polyester, polyethylene terephthalate, polyamides (e.g. nylon), ethylene vinyl alcohol, polystyrene, polyurethane, polybutylene, and polybutylene terephthalate. However, polyolefin polymers are preferred such as, for example, polymers of ethylene and propylene as well as copolymers, terpolymers and blends thereof; examples include, but are not limited to, linear low density polyethylene (LLDPE) and ethylene-propylenecopolymer blends. The microporous films can comprise elastic or inelastic polymers. However, with elastic microporous films sufficient energy, e.g. heat and/or pressure, should be imparted to "set" the treated region of the film.

Once the breathable microporous film has been formed, that is the fine pore network has been created across the film, the microporous film can be treated to impart zoned or controlled regional breathability to the film. The microporous film can be made in-line or made previously and unwound from a supply roll. Selected regions of the microporous film are treated with sufficient adhesive to at least partially cover or fill the pores of the film, thereby reducing the number and/or size of pores therein and thereby reduce and/or substantially eliminate the breathability previously imparted to the film in the treated region. The breathability is directly dependent upon the thickness of the adhesive (the amount of adhesive continuity, and percentage of coverage), the type of adhesive used, and the type of adhesive application used in applying the adhesive coat layer 424 to the microporous film 412. The thicker or more uniform the adhesive coat layer 424 applied to the microporous film 412, the more pores of the microporous film 412 will be covered or filled, thereby reducing the breathability of the microporous film 412. Thus, the breathability of the microporous film 412 can be varied by varying a combination of any or all of the following factors: the thickness of the adhesive coat layer 424 (the amount of adhesive continuity and percentage of coverage), the type of adhesive used in the adhesive coat layer 424, and the type of adhesive application used to apply the adhesive coat layer 424 to the microporous film 412.

The treated regions of the film extend at least 3 cm in the CD and MD and more desirably at least 5 cm×5 cm in the CD and MD. Further, the treated regions of the surface can extend at least 10 cm in either the CD or MD direction. In a further aspect of the invention, the treated regions desirably comprise from about 5% to about 90% of the area of the film. In a preferred embodiment of the present invention the treated regions comprise a contiguous area comprising from about 5% to about 75% of the area of the overall film and more desirably comprise from about 15% to about 60% of the area of the film. In a further embodiment, the regions can comprises a plurality of regions of intermediate and low breathability. The regions of low and intermediate breathability desirably form a single contiguous area and which can, in one aspect, be disposed about the central portion of the film. However, the treated regions can comprise several non-contiguous regions and needs not be centered on the breathable film 412.

Figure 1B:
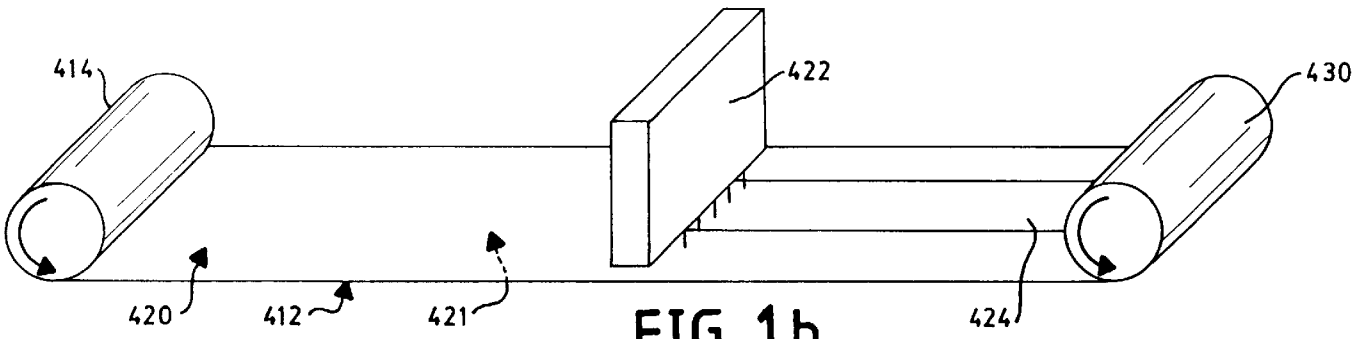
FIG. 1*b* is a schematic representation of an exemplary adhesive applicator assembly suitable for use in practicing the present invention and a zone treated film made therefrom.
Figure 3A:
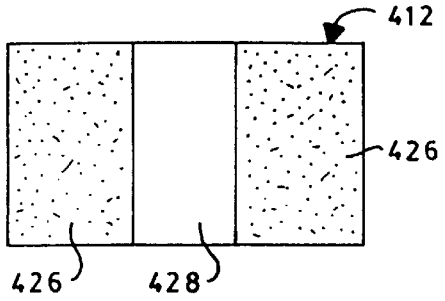
FIG. 3*a* is a plan view of a zone treated microporous film suitable for use in a practicing the present invention.
Figure 3B:
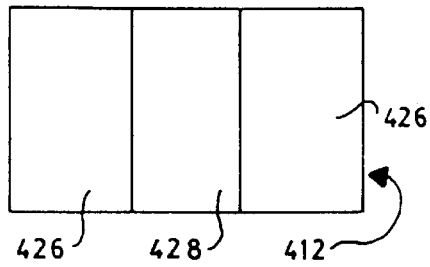
FIG. 3*b* is a plan view of a zone treated microporous film suitable for use in a practicing the present invention.

In one embodiment of the present invention, the adhesive coat layer 424 can be applied in a continuous pattern as seen in second regions 428 in FIG. 1*a*. The adhesive coat layer 424 can also be applied such that a continuous second region 428 is disposed in the center of the microporous film 412, creating a zoned breathability microporous film 412, such as shown in FIGS. 3*a* and 3*b* having highly breathable regions 426 adjacent the opposed edges of the film and a central second region 428 of reduced breathability therebetween. The reduced breathability region 428 can extend continuously in the machine direction of the microporous film. In a further aspect of the invention, the thickness (amount or percentage of coverage) of the adhesive coat layer 424 can be varied in order to further modify the breathability of the corresponding region of the film. Varying the thickness of the adhesive coat layer 424 results in varied levels of breathability extending in the machine direction.

Varying the thickness (including amount or percentage of coverage by the adhesive coat layer 424) is one method of controlling the breathability of the microporous film 412. Other methods include changing the method of application of the adhesive coat layer 424. For example, a meltblown application of 3.2 gsm of adhesive onto the microporous film 412 has very little effect on the WVTR of the microporous film 412. However, the slot coating application of 3.2 gsm of adhesive onto the microporous film 412 has a marked effect on the WVTR of the microporous film 412.

Figure 5A:
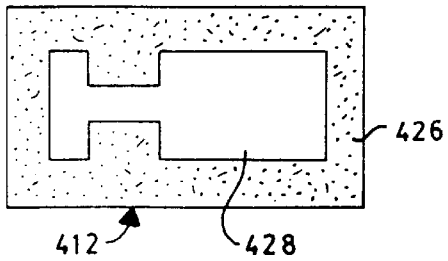
FIG. 5*a* is a plan view of a zone treated microporous film suitable for use in a practicing the present invention.
Figure 5B:
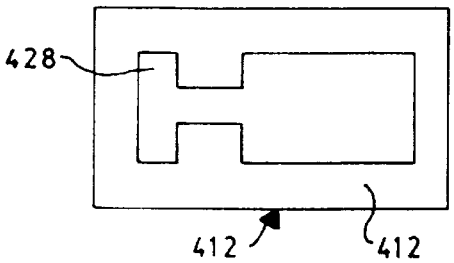
FIG. 5*b* is a plan view of a zone treated microporous film suitable for use in a practicing the present invention.

In a further aspect of the invention, the adhesive coat layer 424 can be applied so as to create shaped regional breathability to the microporous film. In reference to FIGS. 5*a* and 5*b* the adhesive coat layer 424 can be applied in second regions 428 having different WVTRs. Thus, the microporous film 412 is thereby created having first region 426 and second region 428 wherein first region 426 has a higher WVTR than second region 428. The narrow sections, second region 428, can be treated to have a higher or lower WVTR than wide sections, third region 429.

Figure 4A:
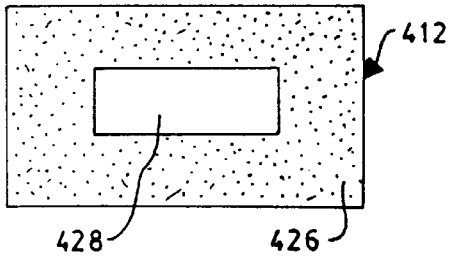
FIG. 4*a* is a plan view of a zone treated microporous film suitable for use in a practicing the present invention.
Figure 4B:
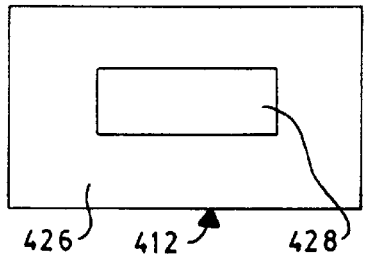
FIG. 4*b* is a plan view of a zone treated microporous film suitable for use in a practicing the present invention.
Figure 6:
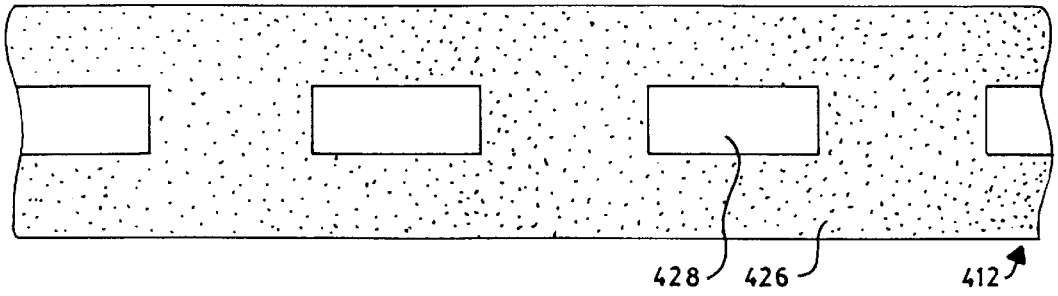
FIG. 6 a schematic representation of an adhesive application pattern suitable for use in practicing the present invention.

In a further aspect, the application of the adhesive coat layer 424 can be discontinuous in the sense that the adhesive is applied in a broken pattern as shown in FIGS. 4*a* and 4*b* and in FIG. 6. The treatment of a microporous film 412 as such create first region 426 and second region 428 whereby first region 426 has greater breathability than second region 428. Further, second region 428 will be separated by portions of first region 428 in the machine direction.

Figure 7:
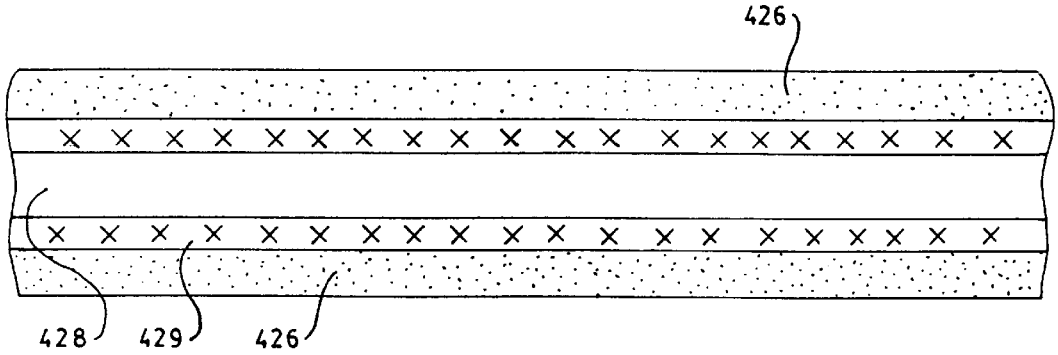
FIG. 7 is a schematic representation of an adhesive application pattern suitable for use in practicing the present invention.

As a further example, the adhesive coat layer 424 can be applied in a manner to create a breathability gradient across the CD of the film. In reference to FIG. 7, one such configuration can result in a zoned breathable film 412 having a first region 426 of high breathability, second region 428 of low breathability and third region 429 of intermediate breathability. The adhesive coat layer 424 applied in the second region 428 is thicker (an increased amount or a higher percentage of coverage of the adhesive coat layer 424) than the adhesive coat layer 424 applied the third region 429, resulting in a breathability gradient. By varying the thickness of the adhesive coat layer 424 in the CD of the microporous film 412, a breathability gradient having regions of varied breathability across the CD of the microporous film 412 is created as opposed to substantially distinct regions of breathability.

As a further example, the adhesive coat layer 424 can be applied in a manner to create a breathability gradient across the CD of the film. In reference to FIG. 7, one such configuration can result in a zoned breathable film 412 having a first region 426 of high breathability, second region 428 of low breathability and third region 429 of intermediate breathability. The adhesive coat layer 424 applied in the second region 428 is of a different type of adhesive for use in the adhesive coat layer 424 applied in the third region 429, resulting in a breathability gradient. By varying the type of the adhesive coat layer 424 in the CD of the microporous film 412, a breathability gradient having regions of varied breathability across the CD of the microporous film 412 is created as opposed to substantially distinct regions of breathability.

As a further example, the adhesive coat layer 424 can be applied in a manner to create a breathabilitygradient across the CD of the film. In reference to FIG. 7, one such configuration can result in a zoned breathable film 412 having a first region 426 of high breathability, second region 428 of low breathability and third region 429 of intermediate breathability. The adhesive coat layer 424 applied in the second region 428 under a different method of adhesive application of the adhesive coat layer 424 than used to apply the adhesive coat layer 424 to the third region 429, resulting in a breathability gradient. By varying the type of adhesive application of the adhesive coat layer 424 in the CD of the microporous film 412, a breathability gradient having regions of varied breathability across the CD of the microporous film 412 is created as opposed to substantially distinct regions of breathability.

The zoned treatment of the microporous film 412 acts to at least partially cover or fill the pores of the microporous film 412, thereby reducing the number or size of the pores in the treated regions thereby reducing the WVTR or breathability in those same regions. In reference to FIGS. 2*a* and 2*b,* the zone treated microporous film can have a first substantially untreated region 426 which has a higher level of breathability than the second adhesively treated region 428 of the microporous film. It is understood that the phrase "substantially untreated region" refers herein to regions that may have undergone a treatment, however the treatment had little or no effect on the WVTR of the microporous film 412. The second region 428 will substantially correspond to those areas of the microporous film to which an adhesive coat layer 424 has been applied.

In a further aspect of the invention, the zoned breathability microporous film can be joined with one or more additional layers. Alternatively, additional layers can be attached to the microporous film prior to zone treating the film. Desirably the microporous film is attached to a pliable support layer capable of being laminated to the film such as, for example, a pliable fibrous, film and/or foam material. Exemplary fibrous layers include, but are not limited to, nonwoven webs, multilayer nonwoven laminates, scrims, woven fabrics, slit films and/or other like materials. Desirably the support fabric comprises one or more layers of spunbonded and/or meltblown fiber webs including, but not limited to, monocomponent spunbond fiber webs, multicomponent spunbond fiber webs, split fiber webs, multilayer nonwoven laminates, bonded carded webs and the like. Typically, these fibrous layers are highly breathable and do not impair the breathability of the microporous film when attached to the microporous film. Generally, the composition of the fibrous layer may be selected to achieve the desired properties, i.e. hand, aesthetics, tensile strength, cost, abrasion resistance, hook engagement, etc. It is understood that the bonding means used to attach the fabric layer to the microporous film should not impair the breathability of the microporous film. This concern is not as great in areas where reduced WVTR is desired.

Further, the fibrous layer can also be treated such as, for example, by embossing, hydroentangling, mechanically softening, printing or treated in another manner in order to achieve additional desired characteristics. In one embodiment the outer layer may comprise about a 10 g/m$^2$ to about 68 g/m$^2$ web of spunbonded polyolefin fibers and even more desirably a 10 g/m$^2$ to about 34 g/m$^2$ web of such fibers. The fibrous layer can be attached or laminated to the microporous film by adhesive bonding, thermal bonding, ultrasonic bonding or other means known in the art. In one aspect of the invention the microporous film and fibrous layer are bonding with an adhesive sprayed via a standard meltblown die to either the nonwoven fabric and/or film. In a further aspect of the invention, the fibrous layer and microporous film can be laminated via thermal point bonding.

The microporous films of the present invention having controlled regional breathability can be used with a wide variety of products or as components of products such as, for example, in personal care articles, infection control products, protective covers, garments and the like. As a particular example, a microporous film similar to that shown in to FIGS. 2*a,* 2*b,* 3*a,* 3*b,* 4*a,* 4*b,* 5*a,* 5*b,* 6, and 7 can be readily converted and incorporated within a breathable barrier of a diaper or incontinence garment whereby the regions of reduced breathability of the microporous film extend along the central portion or crotch of the diaper. The regions more or less coextensive with the absorbent pad are typically of lower breathability, while regions typically of higher breathability extend along the outer portions or "ears" of the garment where the absorbent core is typically not present to maximize dryness or skin health In a further example, the zoned breathability microporous films may be used in surgical gowns. It is believed that the regions of reduced breathability, particularly areas where breathability has been significantly or almost completely reduced, may provide improved barrier properties. For example, areas of reduced breathability are believed to provide improved barrier properties to blood bome pathogens. Thus, surgical gowns can be fabricated employing the treated or low breathability regions within high risk areas, such as the forearms of the gown, and higher WVTR regions within lower risk areas. The microporous film can also be advantageously utilized in numerous other applications employing breathable barrier fabrics.

Figure 8:
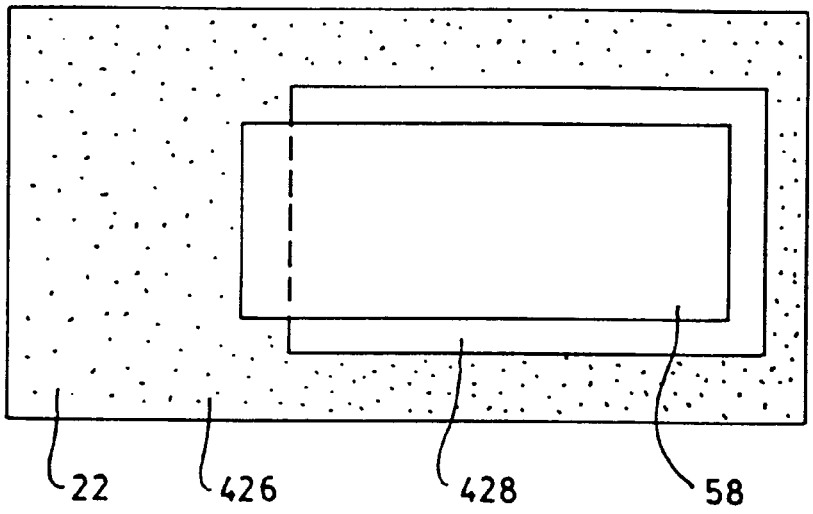
FIG. 8 is a plan view of a zone treated microporous film suitable for use in practicing the present invention and placement of an absorbent pad thereon.
Figure 9:
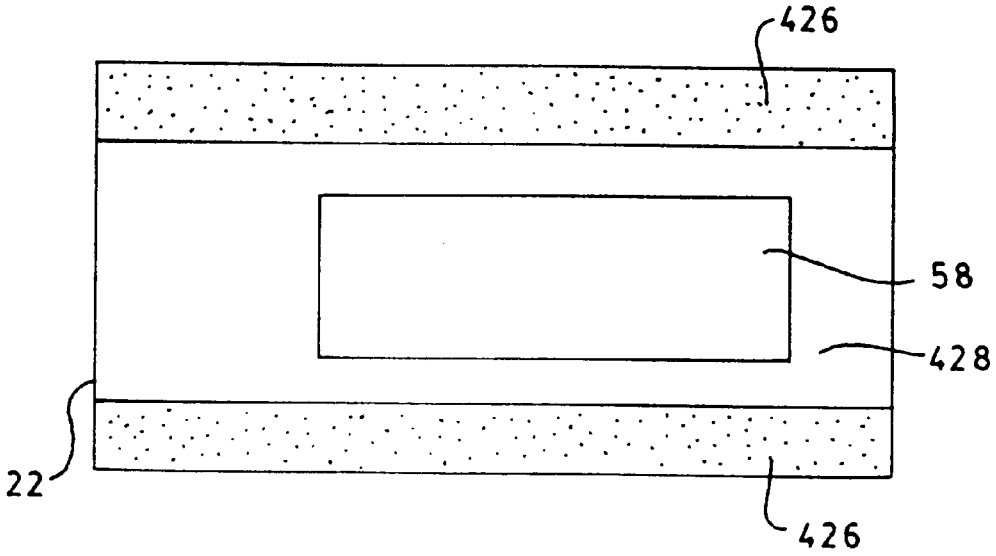
FIG. 9 is a plan view of a zone treated microporous film suitable for use in practicing the present invention and placement of an absorbent pad thereon.
Figure 10:
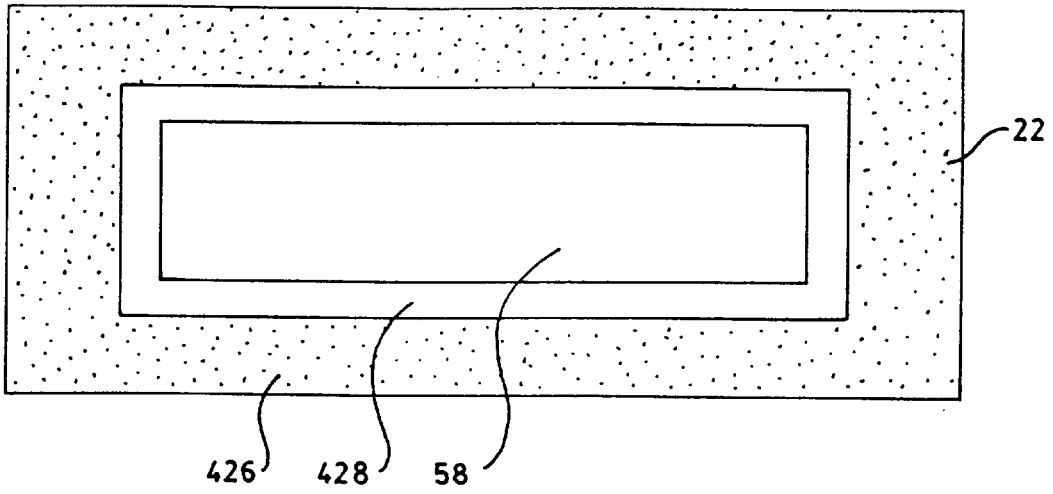
FIG. 10 is a plan view of a zone treated microporous film suitable for use in practicing the present invention and placement of an absorbent pad thereon.
Figure 11:
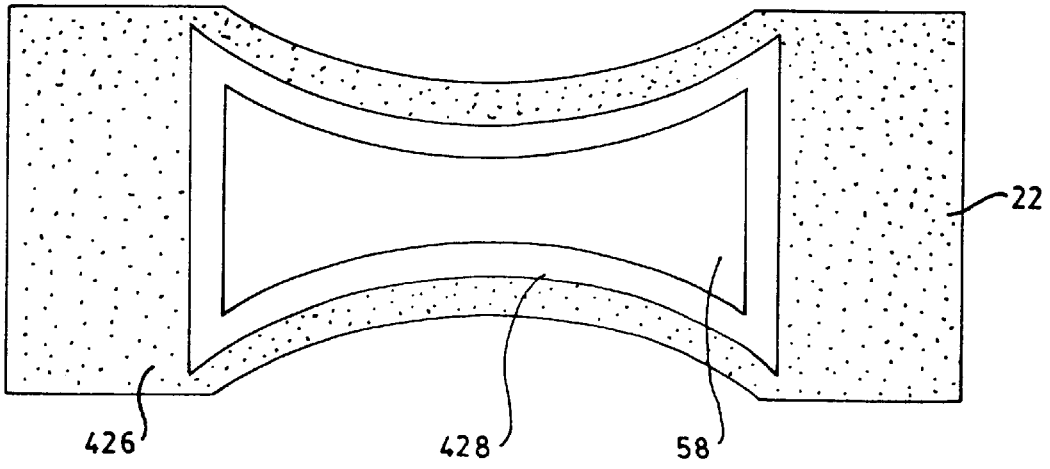
FIG. 11 is a plan view of a zone treated microporous film suitable for use in practicing the present invention and placement of an absorbent pad thereon.

FIG. 8 shows that the absorbent pad 58 need not cover the entire second region 428 and that the absorbent pad 58 may overlap onto a portion of the first region 426. Typically the portion of the absorbent pad which has the highest aqueous liquid loading is positioned over the second region 428. FIG. 9 shows the zone treated microporous film 412 of FIGS. 1*a* and 2*a* including an absorbent pad 58 having smaller dimensions than the second region 428. FIGS. 4*a* and 6 show such microporous film 412. FIG. 11 shows an alternate embodiment as shown in FIG. 10 including a shaped backing member 22 and absorbent pad 58 which have leg cutouts typically included for improved fit and comfort. (See FIGS. 5*a* and 5*b*). However, the size and/or shape of the absorbent pad 58 may coincide with the size and/or shape of the second region 428.

In some embodiments, the present invention is a method of making a film 412 having regions of varied breathability. The method comprises: providing a microporous film 412 wherein said microporous film 412 has a hydrohead of at least 50 mbars and a WVTR of at least 800 g/m$^2$/24 hours; selectively applying adhesive to a portion of said film 412 thereby creating first and second regions 426 and 428 within said film, said second region having dimensions of at least 3 cm by 3 cm wherein the WVTR is decreased within the second region 428 of the film 412 relative to the WVTR of the first region 426.

Variations of the present invention in other embodiments may include any of the following: The step of providing the microporous film 412 may comprise the steps of extruding a film comprising a thermoplastic polymer and a filler, and stretching said film wherein a plurality of pores are created throughout said film 412. The application of adhesive may decrease the WVTR of the second region 428 by at least 25% and further wherein the second region 428 has a minimum dimensions of 5 cm by 5 cm. The second region 428 may comprise from about 5% to about 75% of the area of the film 412. The thermoplastic polymer may comprise a polyolefin polymer and wherein the basis weight of each of said first and second regions 426 and 428 may be below about 35 g/m$^2$. The adhesive may be selectively applied to the microporous film 412 in a coat layer. The second region 428 may comprise between about 5% and 75% of the area of the film 412 and further wherein the first and second regions 426 and 428 of the microporous film 412 each have a basis weight less than about 35 g/m$^2$. The step of providing the microporous film 412 may further comprise the steps of extruding a film comprising a thermoplastic polymer and a filler and stretching the film 412 wherein said stretched filled film may have a basis weight less than about 35 g/m$^2$ and a WVTR in excess of 1500 g/m$^2$/24 hours and further wherein the WVTR of the second region 428 may be decreased by at least 50%. For example, the adhesive applied to the film 412 may comprise a first thickness and a second thickness wherein the first region 426, the second region 428, and the third region 429 may be created within the film 412 with the third region having a WVTR intermediate to the WVTR of the first and second regions 426 and 428. The second region 428 may comprise from about 5% to about 75% of the film 412. The second region 428 and the third region 429 may be continuous. The film 412 may have a WVTR gradient. The method may further comprise the step of laminating a nonwoven web to the film 412 prior to applying the adhesive.

TEST METHODS

Hydrohead:

A measure of the liquid barrier properties of a fabric is the hydrohead test. The hydrohead test determines the height of water or amount of water pressure (in millibars) that the fabric will support before aqueous liquid passes therethrough. A fabric with a higher hydrohead reading indicates it has a greater barrier to aqueous liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as noted below. The hydrohead was determined using a hydrostatic head tester available from Marl Enterprises, Inc. of Concord, N.C. The specimen is subjected to a standardized water pressure, increased at a constant rate until the first sign of leakage appears on the surface of the fabric in three separate areas. (Leakage at the edge, adjacent clamps is ignored.) Unsupported fabrics, such as a thin film, are supported to prevent premature rupture of the specimen.

WVTR:

The water vapor transmission rate (WVTR) for the sample materials was calculated in accordance with ASTM Standard E96-80. Circular samples measuring three inches in diameter were cut from each of the test materials and a control which was a piece of CELGARD™ 2500 film from Hoechst Celanese Corporation of Sommerville, N.J. CELGARD™ 2500 film is a microporous polypropylene film. Three samples were prepared for each material. The test dish was a number 60-1 Vapometerpan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C.) for 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

$$\text{Test WVTR}=(\text{grams weight loss over 24 hours})\times 315.5\ \text{g/m}^2/24\ \text{hours} \quad \text{(I)}$$

The relative humidity within the oven was not specifically controlled.

Underthe predetermined set conditions of 100° F. (32° C.) and ambient relative humidity, the WVTR for the CELGARD™ 2500 control has been defined to be 5000 grams per square meter for 24 hours. Accordingly, the control sample was run with each test and the preliminary test values were corrected to set conditions using Equation (II) below:

$$\text{WVTR}=(\text{Test WVTR/control WVTR})\times(5000\ \text{g/m}^2/24\ \text{hours}) \quad \text{(II)}$$

Strip Tensile:

The strip tensile test measures the peak and breaking loads and peak and break percent elongations of a fabric. This test measures the load (strength) in grams and elongation in percent. In the strip tensile test, two clamps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Results are reported as an average of three specimens and may be performed with the specimen in the cross direction (CD) or the machine direction (MD).

EXAMPLE I

A microporous polyethylene film was laminated to a non-woven fabric to form an outer cover. Adhesive was then added to the film side of the outer cover laminate (which faces the wearer's body when incorporated in an absorbent garment) to create two breathable zones. Adhesive applied through a meltblown application at a level of 3.2 gsm was applied continuously, the full length of the article. A second adhesive head was used to apply adhesive, generally the length and width of the absorbent core, through a slot die at the same and higher add-on rates. The first adhesive system had minimal effect on the film WVTR while the second substantially reduced it. The adhesive used has designation 34-5610 from National Starch and Chemical Company in Bridgewater, N.J.

| Laminate WVTR | WVTR After Meltblown Adhesive Applic. 3.2 gsm | WVTR After Slot Coated Adhesive Applic. 3.2 gsm | WVTR After Slot Coated Adhesive Applic. 6.4 gsm |
|---|---|---|---|
| 4,136 | 3,899 | 3,087 | 2,414 |
| 4,232 | 3,933 | 3,028 | 2,332 |

(WVTR units g/m2/24 hours)

EXAMPLE II

Figure 12:
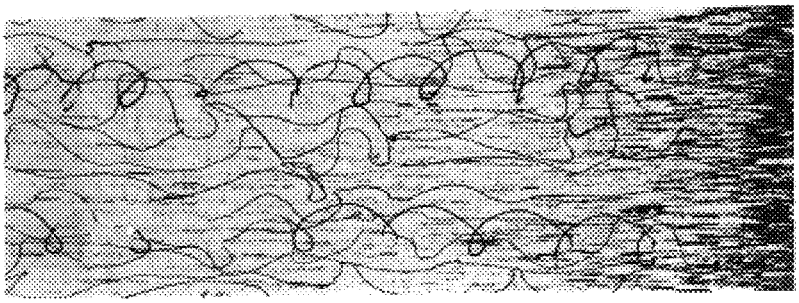
FIG. 12 is a plan view representation of a treated microporous film leaving an open adhesive pattern with minimal effect on the WVTR of the film.
Figure 13:
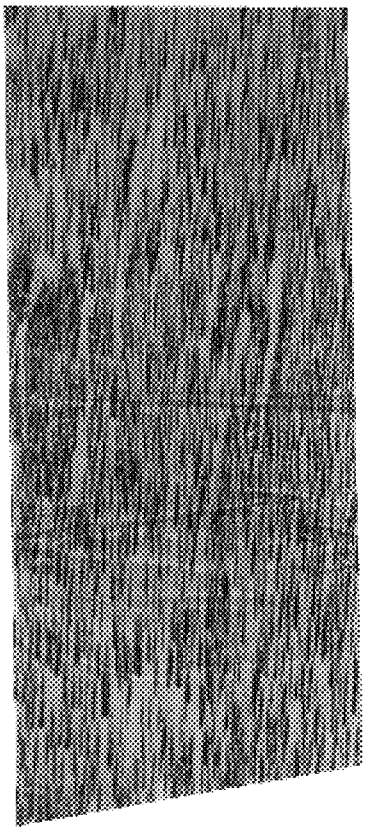
FIG. 13 is a plan view representation of a treated microporous film having an adhesive coat layer with significant reduction of the WVTR of the film.
Figure 14:
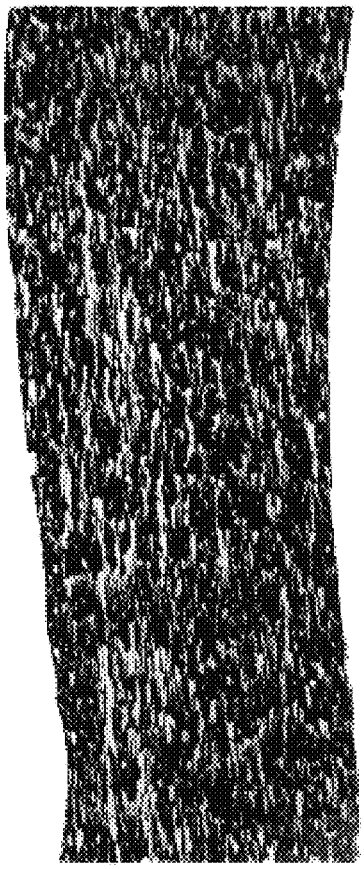
FIG. 14 is a plan view representation of a treated microporous film having an adhesive coat layer with significant reduction of the WVTR of the film.

Referencing the WVTR data in Example I, FIG. 12 shows a breathable film with a meltblown adhesive coverage of about 8%. This resulted in the WVTR dropping from about 4200 to about 3900. FIG. 13 shows a breathable film with a coat layer coverage of about 24% resulting in about a 1000 drop in WVTR. FIG. 14 shows a 70% coat layer coverage which resulted in a WVTR drop of about 1800.

EXAMPLE III

It has been found that slot coating applied to a non-woven web has less effect on the laminate WVTR than applying to the film. A slot coater, therefore could be used to maintain high WVTR in the desired product regions if slot coating is applied to a non-woven like fabric rather than onto the film.

An equal amount of construction adhesive (34-561 0 from National Starch and Chemical Company in Bridgewater, N.J.) was applied via slot coating onto both a non-woven fabric (0.75 osy, sheath/core, 50/50 polypropylene polyethylene spunbond) and a microporous polyethylene film with a WVTR of approximately 4,270. The examples show the smaller reduction in WVTR when the non-woven was slot coated compared to when the film was slot-coated.

| Film WVTR | Laminate WVTR When Slot Coated onto Non-woven |
|---|---|
| 4,270 | 4,080 |
| **Laminate WVTR** | **WVTR When Slot Coated onto Film** |
| 4,080 | 3,500 |

EXAMPLE IV

It has been found that neither a meltblown (also referred to as MB) nor swirl adhesive application lower the WVTR of the microporous film significantly at adhesive levels up to 3.2 gsm of 34-5610 adhesive.

| Description | WVTR |
|---|---|
| Film | 4,266 |
| 3.2 gsm MB on nonwoven | 4,178 |
| 1.6 gsm MB on film | 4,317 |
| 3.2 gsm Swirl on film | 4,063 |
| 1.0 gsm Swirl on film | 4,486 |

EXAMPLE V

This example demonstrates that high WVTR values can result in condensation of water vapor on the outer surface of an absorbent garment. This is perceived as leakage by many consumers.

Panelists evaluated the materials in a blind comparison using the following test method. Before evaluation, all samples were loaded with 240 ml of body temperature saline, and placed on a heating pad also warmed to body temperature for two hours. Each diaper was placed inside a black box for a blind evaluation. All participants evaluated each material by feeling it four times as presented to them in a randomly ordered sequence. Each material was evaluated independently. Each of the two studies included three codes. In each study panelists evaluated a total of twelve diapers (3 codes×4 repeats=12 diapers) with a fifteen minute break after evaluating six diapers to help reduce hand fatigue.

| Product | WVTR of Outer Cover | Front Moisture Rating | Back Moisture Rating |
|---|---|---|---|
| A | 1,650 | 15.9 | 22.1 |
| B | 2,715 | 18.8 | 24.1 |
| C | 4,125 | 20.9 | 26.3 |
| D | 0 | 12 | 18 |

Products A, B, C, and D were commercially available diapers in which the outer covers were replaced with over covers having the stated WVTR.

EXAMPLE VI

This example demonstrates that high WVTR levels in nonabsorbent areas of a disposable garment increase wearer comfort. The disposable garments tested were commercially available DEPENDS® Undergarments. The test was conducted on a KES-F7 Thermo-Lobo IIB Type equipment available from Kato-Tech Co., LTD., in Kyoto, Japan. The test method is described in the operating manual for the equipment. Outer covers of differing breathability were tested.

The ability of moisture and heat to permeate through fabric is a significant factor in determining how comfortable a garment will be. Heat can be transferred through a fabric in two ways: dry heat transfer and/or moisture-assisted heat transfer. From the dry and wet heat transfer rate measurements, the permeability index (Im), can be calculated. The KES Thermo-labo test measures the dry and wet heat transfer rates of a material using a guarded or sweating hot plate. It also measures how warm or cool a material feels to the touch and the thermal conductivity of materials.

The characteristic values shown from the KES Thermo-labo test are described below.

Wet Heat Transfer represents the amount of heat that is transferred from the skin through the fabric to the outside environment with the assistance of moisture. The larger the wet heat transfer value, the more heat will be lost or transferred through the fabric with the assistance of moisture. This test is appropriate for the measurement of heat transfer in most situations where the wearer would perspire.

Im or Permeability Index is the ratio of the thermal and evaporative resistance of the fabric to the ratio of thermal and evaporative resistance of air. As the value approaches 1, the less resistant or more air-like the fabric is. For example, a lightweight, loosely woven fabric would have a larger Im value than Tyvek. (Differences as small as 0.01 can be perceived.)

| Woven Cotton | Non-breathable non-microporous film | 1,200 WVTR microporous film | 2,500 WVTR microporous film | 3.5 osv |
|---|---|---|---|---|
| Wet Heat Transfer (Watts/m2) | 7.72 | 8.87 | 11.94 | 18.4 |
| IM or Permeability Index | 0.18 | 0.23 | 0.39 | 0.59 |

EXAMPLE VII

This example demonstrates that high WVTR levels in certain areas of a disposable garment increase wearer skin wellness by reducing skin occlusion and excessive hydration of the skin.

Undergarments that were modifications of commercially available DEPEND® Undergarments, were tested with 20 panelists. The modifications included shortening the absorbent core from 21 inches to 19 inches (centered on the outer cover) and incorporating new outer covers with the stated WVTRs. The outer covers consisted of a film (either nonporous or microporous) and a nonwoven laminated to the film.

Skin conductance measurements were taken on the panelist's lower back in a region where the garment's body-side liner and outer cover covered the skin (not in a region where the absorbent core was present).

The skin conductance readings were taken with a Skicon 200 instrument such as that available from ACA DERM of Mento Park, Calif. Panelists were given a short sleeve disposable lab coat, made of polypropylene spunbond, cotton sweatpants, and a pair of cotton underwear to wear during the test period. Panelists were then allowed to acclimate to the environment which was controlled to approximately 72° F./43% R.H. for 10–15 minutes. After acclimation, the panelists lay on their stomachs, their clothing over their lower back was peeled down, and a Baseline skin conductance reading was taken using the Skicon.

Subsequently, the panelists were given an undergarment to don, under their underwear and sweatpants. The total wear time of the undergarment was 1.5 hours. During the first ten minutes of wear time, the panelists participated in a moderate exercise of their choice (such as walking, treadmill, stationary bike, aerobic activity). The next twenty minutes, the panelists rested. They exercised the next ten minutes (3040 minutes into wear time), rested the next 20 minutes (40–60 minutes into weartime), exercised the next ten minutes (60–70 minutes into wear time), and finally rested the last twenty minutes of the 1.5 hour undergarment weartime.

After the 1.5 hour wear time, a post-wear skin conductance reading was taken in the same manner and region as the baseline reading.

The change in skin conductance, from the baseline to post wear regions, represents the change in skin hydration during that period. The data shows that the non-breathable product resulted in a much greater increase in skin hydration than the breathable products. Such increases over time lead to wearer discomfort and reduced skin wellness.

| | Baseline Skin Surface Moisture Reading | Post wear Skin Surface Moisture Reading | Change in Skin Surface Moisture Reading after Wear Time |
|---|---|---|---|
| Non-breathable non-microporous film | 220 | 1,187 | 967 |
| 2,500 WVTR microporous film | 222 | 376 | 154 |
| 3,700 WVTR microporous film | 239 | 364 | 125 |

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

What is claimed is:

1. A method of making a film having regions of varied breathability comprising: providing a microporous film wherein said microporous film has a hydrohead of at least 50 mbars and a WVTR of at least 800 g/m$^2$/24 hours; selectively applying adhesive to a portion of said film thereby creating first and second regions within said film, said second region having dimensions of at least 3 cm by 3 cm and wherein the porosity and the WVTR is decreased within said second region of the film relative to the WVTR of the first region.

2. The method of claim 1 wherein providing said microporous film comprises the steps of extruding a film comprising a thermoplastic polymer and a filler and stretching said film wherein a plurality of pores are created throughout said film.

3. The method of claim 2 wherein the application of adhesive decreases the WVTR of the second region by at least 25% and further wherein said second region has a minimum dimensions of 5 cm by 5 cm.

4. The method of claim 3 wherein said second region comprises from about 5% to about 75% of the area of said film.

5. The method of claim 4 wherein said thermoplastic polymer comprises a polyolefin polymer and wherein the basis weight of each of said first and second regions is below about 35 g/m$^2$.

6. The method of claim 1 wherein said adhesive is selectively applied to said microporous film in a coat layer.

7. The method of claim 6 wherein said second region comprises between about 5% and 75% of the area of said film and further wherein said first and second regions of said microporous film each have a basis weight less than about 35 g/m$^2$.

8. The method of claim 7 wherein providing said microporous film comprises the steps of extruding a film comprising a thermoplastic polymer and a filler and stretching said film wherein said stretched filled film has a basis weight less than about 35 g/m$^2$ and a WVTR in excess of 1500 g/m$^2$/24 hours and further wherein said WVTR of said second region is decreased by at least 50%.

9. The method of claim 1 wherein said adhesive applied to said film comprises a first thickness and a second thickness wherein first, second, and third regions are created within said film with said third region having a WVTR intermediate to the WVTR of said first and second regions.

10. The method of claim 9 wherein said second region comprises from about 5% to about 75% of said film.

11. The method of claim 10 wherein said second and third regions are continuous.

12. The method of claim 11 wherein said film has a WVTR gradient.

13. The method of claim 4 further comprising the step of laminating a nonwoven web to said film prior to applying said adhesive.

* * * * *